US00PP35762P2

(12) United States Plant Patent
Carter

(10) Patent No.: US PP35,762 P2
(45) Date of Patent: Apr. 16, 2024

(54) ***SALVIA* PLANT NAMED 'IGNITION SUNRISE'**

(50) Latin Name: ***Salvia* x *jamensis***
Varietal Denomination: Ignition Sunrise

(71) Applicant: Kermit E. Carter, Elk, CA (US)

(72) Inventor: Kermit E. Carter, Elk, CA (US)

( * ) Notice: Subject to any disclaimer, the term of this patent is extended or adjusted under 35 U.S.C. 154(b) by 0 days.

(21) Appl. No.: 18/183,157

(22) Filed: Mar. 14, 2023

(51) Int. Cl.
*A01H 5/02* (2018.01)
*A01H 6/50* (2018.01)

(52) U.S. Cl.
USPC ..... Plt./475

(58) Field of Classification Search
USPC ..... Plt./475
CPC ... A01H 5/02; A01H 5/12; A01H 5/00; A01H 6/508; A01H 6/50
See application file for complete search history.

(56) References Cited

U.S. PATENT DOCUMENTS

PP19,820 P3 * 3/2009 Worley ..... A01H 6/508 Plt./475
PP20,680 P2 * 1/2010 Smith ..... A01H 5/12 Plt./475
PP33,084 P2 * 5/2021 Solano Ramirez ..... Plt./475

OTHER PUBLICATIONS

Wright California Spring Trials 2022 Greenhouse Grower, retrieved on Jul. 6, 2023 at https://www.greenhousegrower.com/crops/ornamentals/california-spring-trials-2022-planthaven-pacific-plug-liner-and-suntory-flowers-rock-new-plants-at-santa-barbara-polo-club/#slide=159111-159122-2, 4 pp. (Year: 2022).*

* cited by examiner

*Primary Examiner* — June Hwu
(74) *Attorney, Agent, or Firm* — Weatherly IP Solutions, LLC; James M. Weatherly

(57) ABSTRACT

A new cultivar of *Salvia* named 'Ignition Sunrise' that is distinguishable by contrasting cream and rose-pink bicolored flowers which are borne early and freely on compact plants with mid-green semi-glossy leaves, is disclosed.

2 Drawing Sheets

Genus and species: *Salvia* x *jamensis.*
Variety denomination: 'Ignition Sunrise'.

BACKGROUND

The present disclosure relates to a new and distinct cultivar of *Salvia* plant, also known as a sage, a perennial that is grown for use as an ornamental landscape and container plant. The new variety is known botanically as *Salvia* x *jamensis* and will be referred to hereinafter by the cultivar name 'Ignition Sunrise'.

'Ignition Sunrise' originated and was selected from a population of hybrid seedlings from a *Salvia* breeding program, which was started in 2010. The breeding program was conducted in the inventor's greenhouse nursery in Elk, California. The aim of the breeding program is to develop a uniform series of compact free-flowering varieties of *Salvia* x *jamensis* each with similar plant habits and flowering characteristics but with distinctly different flower colors. 'Ignition Sunrise' was selected by the inventor in 2020 from seedlings which resulted from the controlled hybridization using pollen collected from an unnamed yellow-flowered selection within the inventor's collection of *Salvia* varieties. The inventor applied the collected pollen to plants of the inventor's variety *Salvia* x *jamensis* 'Golden Elk' (not patented). Seed from the female parent, 'Golden Elk' was grown out, and one seedling, named 'Ignition Sunrise' the, was selected for its distinctive bi-colored cream and rose-pink flowers which were borne on compact low-growing plants with mid-green glossy leaves.

'Ignition Sunrise' was first asexually propagated in 2020 in a greenhouse at the inventor's nursery in Elk, California using softwood tip cuttings. The inventor has confirmed that 'Ignition Sunrise' is stable and reproduces true to type in successive generations of asexual reproduction.

SUMMARY

The following traits have been repeatedly observed and represent the distinguishing characteristics of 'Ignition Sunrise'. 'Ignition Sunrise' has not been tested under all possible conditions and phenotypic differences may be observed with variations in environmental, climatic, and cultural conditions, without however, any variance in genotype.

1. 'Ignition Sunrise' exhibits a compact well-branched upright plant habit in its first and second years of growth in a container.
2. After two years growth in-ground, 'Ignition Sunrise' becomes semi-prostrate in habit.
3. The flowers of 'Ignition Sunrise' are bi-colored cream and rose-pink.
4. 'Ignition Sunrise' grows and flowers rapidly. Flowering plants may be produced in 10 to 12 weeks from a cutting.
5. 'Ignition Sunrise' is drought tolerant.

DESCRIPTION OF THE PHOTOGRAPHS

The accompanying color photographs illustrate the overall appearance of the new *Salvia* cultivar 'Ignition Sunrise' showing the colors as true as it is reasonably possible to obtain in colored reproductions of this type. Photographs were taken in March 2022 in Santa Barbara, California from a one year old plant grown outdoors in 3.7-gallon (14 liter) container, with one pinch after initial cutting establishment and without any chemical growth regulators. Colors in the photographs may differ from the color values cited in the detailed botanical description, which more accurately describes the actual colors of the new variety 'Ignition Sunrise'.

DESCRIPTION OF THE NEW VARIETY

Figure 1:
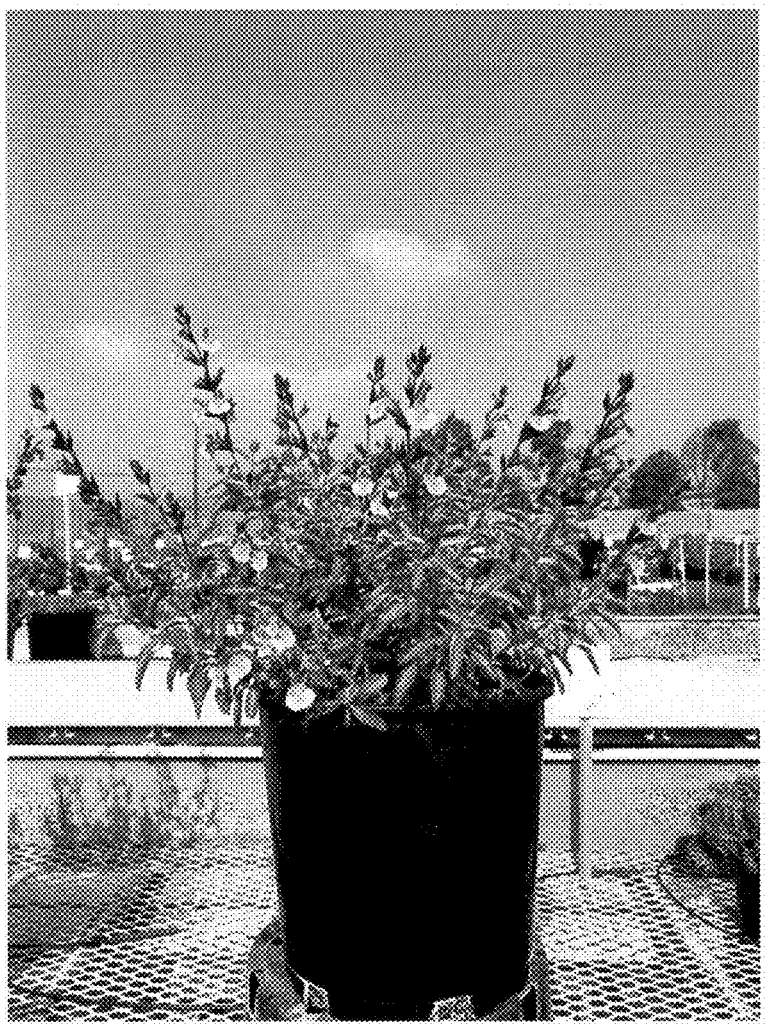
FIG. 1 depicts an entire plant in flower of 'Ignition Sunrise'.
Figure 2:
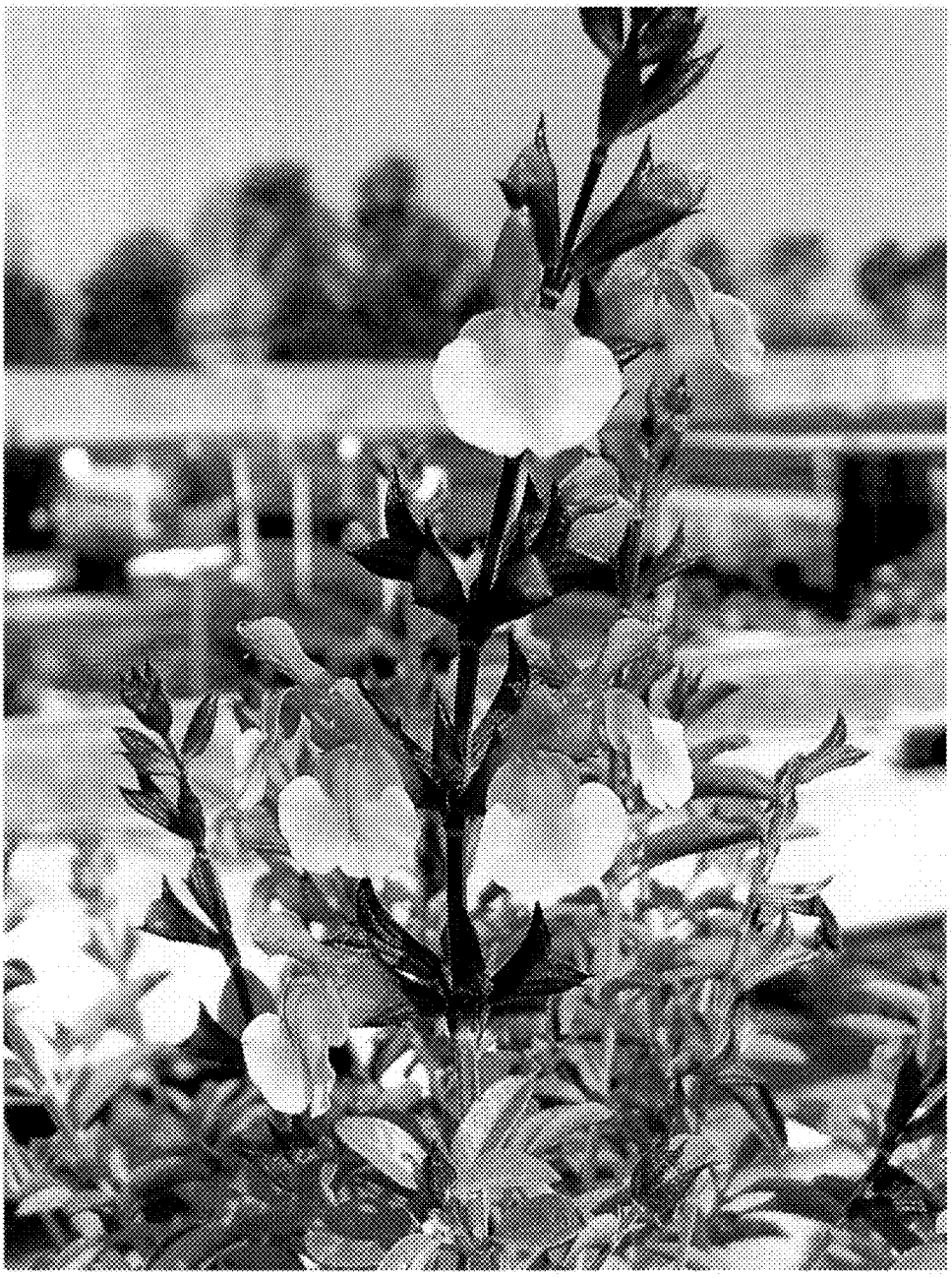
FIG. 2 depicts a close-up view of a young inflorescence of 'Ignition Sunrise' showing its first flowers and the terminal bud cluster.

The following detailed descriptions set forth the distinctive characteristics of 'Ignition Sunrise'. Observations, measurements, values, and comparisons were collected in March 2022 in Santa Barbara, California from a one year old plant which had been growing outdoors in full sun in a 3.7 gallon (14 liter) container in Santa Barbara, California, with one pinch after initial cutting establishment and without any chemical growth regulators. Color determinations were made in accordance with The 2007 Royal Horticultural Society Colour Chart from London England, except where general color terms of ordinary dictionary significance are used.

Classification:

*Family.*—Lamiaceae.
*Genus.*—*Salvia.*
*Species.*—X *jamensis.*
*Common name.*—Sage.

Parentage:

*Female parent.*—*Salvia* x *jamensis* 'Golden Elk'.
*Male parent.*—Unnamed and unreleased proprietary selection.

Plant:

*Propagation method.*—Softwood tip cuttings.
*Rooting system.*—Fine and fibrous.
*Vigor.*—Moderate vigor.
*Time to develop roots.*—5 days are needed for a cutting to develop roots at recommended rooting temperature of 20° to 22° Centigrade.
*Crop time.*—Approximately 12 weeks are required to produce a budded and flowering plant in a quart container from a rooted cutting.
*Suggested container size.*—Quart to 1 gallon container.
*Use.*—Ornamental for use as a landscape plant or container plant.
*Type.*—Perennial.
*Overall dimensions.*—After one year's growth in a 3.7 gallon container, 25 cm in height, including the inflorescence, and 50 cm-55 cm in width.
*Cultural requirements.*—Grow in full sun with moderate water and well-draining soil.
*Hardiness.*—USDA Zone 7.
*Form.*—Upright in first two years of growth; semi-prostrate when later established in the ground.
*Growth habit.*—Compact.
*Blooming season.*—From one month after breaking spring dormancy to first frost.
*Lastingness of blooms.*—Inflorescence has some flower for 14 days, individual flowers last for 2 to 3 days.

Stems (below first pinch):

*Condition.*—Lignified.
*Shape.*—Round.
*Length.*—1 cm to 2 cm.
*Diameter.*—4 mm.
*Bark surface.*—Rough.
*Bark color.*—147A and N200B both present.

Branches:

*Quantity.*—40-45, of which 6-8 are primary branches and 35 or more are secondary branches.
*Branch stem shape.*—Square, corners rounded.
*Branch stem length.*—Up to 15 cm. measured to base of inflorescence.
*Branch stem width.*—1.5 mm.
*Internode length.*—Varies between 25 mm (primary branches), and 9 mm (secondary branches).
*Branch stem color.*—143C except some lower internodes exhibit light anthocyanin coloration, 182C.

Leaves:

*Type, arrangement.*—Simple, opposite.
*Attachment.*—Petiolate.
*Quantity per branch.*—8 to 11 pairs.
*Shape.*—Elliptic.
*Length.*—*Up to* 23 mm.
*Width.*—*Up to* 15 mm.
*Margin.*—Undulating, crenulate, teeth rounded, depth up to 1 mm.
*Thickness.*—Moderate.
*Venation.*—Pinnate, midrib slightly sulcate.
*Vein color* (*adaxial surface*).—137B.
*Vein color* (*abaxial surface*).—N138B, except midrib 138C.
*Texture.*—Adaxial surface: Smooth, glabrous, semi-glossy. Adaxial surface: Smooth, matte.
*Color.*—Adaxial surface: 137B. Abaxial surface: N138B.
*Apex.*—Acute.
*Base.*—Cuneate.
*Fragrance.*—Pleasant sage fragrance when rubbed.
*Stipules.*—Present at lower two or three nodes only. Small, sessile, elliptic, up to 11 mm in length and 5 mm in width. Margins entire, color 137B (adaxial surface), N138B (abaxial surface), surfaces smooth, glabrous.

Petiole:

*Shape.*—Terete.
*Length.*—7 mm.
*Width.*—1 mm.
*Texture.*—Puberulent.
*Color.*—143C.

Peduncle:

*Length.*—25 mm.
*Shape.*—Square.
*Width.*—2 mm.
*Texture.*—Puberulent.
*Color.*—137D.

Inflorescence:

*Type.*—Terminal raceme. Flowers always arranged in opposite pairs to each node.
*Aspect.*—Flowers are outward facing, rotated 75-80 degrees apart, except uppermost flower at tip of inflorescence is erect at approximately 45 degrees from the vertical.

*Inflorescence dimensions*.—Length: 10 cm to 13 cm, width, 5 cm.

*Internode distance*.—Ranges from 14 mm between the lowest (first and second) pair of flowers to 10 mm between the uppermost open flowers.

Pedicel:

*Length*.—4 mm.

*Diameter*.—0.75 mm.

*Texture*.—Smooth, glabrous.

*Color*.—197B.

Calyx:

*Shape*.—Campanulate, flared toward the apex.

*Length*.—13 mm.

*Diameter at base*.—2.5 mm.

*Width*.—10 mm between sepal apices.

Sepals:

*Quantity*.—3, one larger upper sepal, two lower sepals, all longitudinally fused except for sepal apices.

*Shape* (*each sepal when separated*).—Boat shaped, apex acuminate, base truncate, margins entire.

*Dimensions*.—Upper sepal: 12 mm in length, 6 mm in width. Lower sepals: 11 mm in length, 4 mm in width.

*Texture*.—Adaxial surface: Puberulent, longitudinally ribbed. Ribs 1 mm apart, raised less than 0.1 mm. Abaxial surface: Glabrous, longitudinal depressions.

*Color*.—All sepals, adaxial surfaces: Initially, at bud stage, entirely 187B, becoming 147A as flower opens, except apex remains 187B. All sepals, abaxial surfaces: 147A except apex 187B.

Flowers:

*Quantity*.—8 to 10 opposite pairs.

*Shape*.—Tubular, two-lipped.

*Fragrance*.—Pleasant sage fragrance.

*Bracts*.—Flowers are subtended by calyx and sepals. No bracts are present.

Bud:

*Shape*.—Ellipsoidal on emergence from calyx, becoming cylindrical with rounded apex immediately prior to opening.

*Length*.—4 mm on emergence, 16 mm immediately prior to opening.

*Width*.—5 mm on emergence, 6 mm immediately prior to opening.

*Surface*.—Strongly pubescent, especially apex. Hairs dense, fine, 1 mm in length, color 63B.

*Color*.—Emerges N66A, becoming 63B immediately prior to opening.

Corolla:

*Shape*.—Tubular proximally to two-lipped distally, lower lip attitude relative to corolla is strongly downwards.

*Length*.—17 mm including corolla tube.

*Height* (*corolla viewed vertically*).—3 mm- 4 mm.

*Width* (*corolla viewed horizontally*).—2.5 mm.

*Texture*.—Glossy, glandular.

*Color* (*both surfaces*).—63B, except tube base NN155D, translucent.

Petals:

*Quantity*.—2.

*Arrangement*.—One upper petal and one lower petal which appears as a large prominent lip with two outer lateral lobes and two inner lateral lobes all fused to each other.

*Upper petal*.—Shape: Hooded. Length: 11 mm. Width: 4 mm. Texture: Adaxial surface: Pubescent. Hairs dense, fine, 0.5 mm in length, color 63B. Abaxial surface: Glabrous. Apex: Rounded, with cluster of fine hairs approximately 0.5 mm in length, hair color 63B. Base: Truncate with lower lip at corolla mouth. Margin: Smooth, entire. Color: Adaxial surface: 63B. Abaxial surface: 55B.

*Lower petal, lip*.—Shape: Complex, consisting of outer pair of flared approximately circular lobes partially fused to inner pair of elliptical lobes. Length (overall): 16 mm from petal base to outer lobe apex. Width: 20 mm. at widest (across outer lobes). Texture (all lobes, both surfaces): Smooth, matte Apex (outer lobes): Emarginate, depth of notch 1 mm. Base (inner lobes): Truncate. Margin: Smooth, entire, outer lobe margins gently undulating. Color (outer lobes, both surfaces): Cream 8D with light pink veins, 55B, extending from inner lobes. Color (inner lobes, both surfaces): Light pink 55B.

Reproductive organs:

*Stamens*.—Quantity: 2. Length: 13 mm, each filament basally fused for 7 mm and free for 6 mm. Color: Filaments NN155D where fused, becoming 62D. Anthers: Length: 2 mm. Width: 1 mm. Color: 163C.

*Pollen*.—Amount: Moderate. Color: 163B.

*Pistil*.—Quantity: 1. Stigma: Shape: Asymmetrically forked. Length: Longer fork 4 mm, strongly recurved; shorter fork 2 mm, gently recurved. Diameter 0.75 mm. Color: 65D. Style: Length (excluding stigma): 23 mm. Color: N155D becoming darker 65D towards stigma.

*Ovary* (*only observed unfertilized*).—Shape: Elongated ovoid. Dimensions: 3 mm. in length, 1.5 mm in diameter. Color: 151C.

Seed:

*Quantity, shape, dimensions*.—Sparse, ovoid, length 3 mm, diameter 1.5 mm.

*Color*.—Speckled, ranging between 165B and N199B.

*Surface*.—Smooth and matte.

Disease and pest susceptibility: Susceptible to aphids (*aphis gossypii*) when stressed. Generally outgrows most bacterial and viral infections. Resistant to deer and rabbit grazing.

Drought tolerance: Drought tolerant.

COMPARISON WITH PARENTAL LINES AND KNOWN VARIETY

The female parent, 'Golden Elk', exhibits yellow flowers, whereas 'Ignition Sunrise' exhibits cream and rose-pink bicolored flowers with greater contrast than the female parent. In addition, in comparison with 'Golden Elk', 'Ignition Sunrise' exhibits a more compact and low growing plant habit, and a longer flowering period. The flowers of the male parent are single colored yellow and the male parent exhibits a more open plant habit and bears larger flowers and leaves.

The closest variety to 'Ignition Sunrise' known to the inventor is *Salvia* Plant 'Balmirrobi' (U.S. Plant Pat. No. 33,084). Both 'Ignition Sunrise' and 'Balmirrobi' exhibit bicolored flowers in which the upper petal lobe is rose-pink in color. The lower petal lobes of 'Ignition Sunrise' are cream in color, whereas the lower petal lobes of 'Balmirrobi' are white in color. In addition, plants of 'Ignition Sunrise' appear to be more compact than plants of 'Balmirrobi'.

'Ignition Sunrise' exhibits a height of 25 cm. including the inflorescences, whereas 'Balmirrobi' exhibits a height of 32 cm to the top of the foliage and excluding the inflorescences.

The two *Salvia* varieties, 'Dancing Dolls' (U.S. Plant Pat. No. 19,820) and 'Shell Dancer' (U.S. Plant Pat. No. 20,680) both exhibit rose and cream bicolored flowers but are significantly larger and more vigorous in growth habit. Both varieties achieve a height and width of 1 meter to 1.3 meters.

I claim:

1. A new and distinct cultivar of *Salvia* Plant Named 'Ignition Sunrise' as described and illustrated herein.

* * * * *